United States Patent
Fredenberg et al.

(10) Patent No.: US 10,296,808 B2
(45) Date of Patent: May 21, 2019

(54) METHOD AND X-RAY SYSTEM FOR COMPUTER AIDED DETECTION OF STRUCTURES IN X-RAY IMAGES

(71) Applicant: KONINKLIJKE PHILIPS N.V., Eindhoven (NL)

(72) Inventors: Jon Erik Fredenberg, Vallentuna (SE); Mats Vilhelm Lundqvist, Stockholm (SE); Ewald Roessl, Henstedt-Ulzburg (DE); Klaus Erhard, Hamburg (DE); Thomas Koehler, Norderstedt (DE); Bjorn Cederstrom, Stockholm (SE); Hanns-Ingo Maack, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 156 days.

(21) Appl. No.: 14/772,794

(22) PCT Filed: Feb. 20, 2014

(86) PCT No.: PCT/IB2014/059122
§ 371 (c)(1),
(2) Date: Sep. 4, 2015

(87) PCT Pub. No.: WO2014/147495
PCT Pub. Date: Sep. 25, 2014

(65) Prior Publication Data
US 2016/0019432 A1    Jan. 21, 2016

Related U.S. Application Data

(60) Provisional application No. 61/803,906, filed on Mar. 21, 2013.

(51) Int. Cl.
G06K 9/46    (2006.01)
A61B 6/00    (2006.01)
(Continued)

(52) U.S. Cl.
CPC ............ *G06K 9/4671* (2013.01); *A61B 6/482* (2013.01); *A61B 6/502* (2013.01); *G06K 9/52* (2013.01);
(Continued)

(58) Field of Classification Search
None
See application file for complete search history.

(56) References Cited

U.S. PATENT DOCUMENTS 6,226,352 B1    5/2001  Salb
7,315,640 B1    1/2008  Brady et al.
(Continued)

FOREIGN PATENT DOCUMENTS

JP    2006101926    4/2006
JP    2008000190    1/2008

OTHER PUBLICATIONS

Wang, et al., "Synthetic CT: simulating arbitrary low dose single and dual energy protocols", Medical Imaging 2011: Physics of Medical Imaging, SPIE, vol. 7961, No. 1, Mar. 3, 2011.
(Continued)

*Primary Examiner* — Gandhi Thirugnanam (57) ABSTRACT

The present invention relates to X-ray imaging technology as well as image post-processing. Particularly, the present invention relates to a method for computer aided detection of structures in X-ray images as well as an X-ray system. A computer aided detection algorithm visibly determines tissue structures in X-ray image information and subsequently matches the shape of a determined tissue structure with a library of known tissue structures for characterizing the type of determined tissue structure. The determination of a tissue structure and thus the characterization of the type of the tissue structure may be enhanced when employing also spectral information, in particular energy information of the
(Continued)

acquired X-ray image. Accordingly, a method (70,80,90) for computer aided detection of structures and X-ray images is provided, comprising the steps of obtaining (72) spectral X-ray image information of an object, wherein the spectral X-ray image information constitutes at least one X-ray image, detecting (74) a tissue structure of interest in the X-ray image by employing a computer aided detection algorithm, wherein detecting a tissue structure of interest in the X-ray image comprises the computer aided detection algorithm being adapted to evaluate the X-ray image for tissue structure shape and compare the tissue structure shape with a plurality of pre-determined tissue structure shapes and wherein the computer aided detection algorithm is adapted to evaluate spectral information of the X-ray image for detecting the tissue structure of interest.

19 Claims, 4 Drawing Sheets (51) Int. Cl.
*G06T 5/50* (2006.01)
*G06K 9/52* (2006.01)
*G06K 9/62* (2006.01)
*G06T 7/00* (2017.01)
*G06T 7/60* (2017.01)

(52) U.S. Cl.
CPC .............. *G06K 9/6201* (2013.01); *G06T 5/50* (2013.01); *G06T 7/0012* (2013.01); *G06T 7/60* (2013.01); *G06T 2207/10116* (2013.01); *G06T 2207/30068* (2013.01); *G06T 2207/30242* (2013.01)

(56) References Cited

U.S. PATENT DOCUMENTS

| | | | |
|---|---|---|---|
| 7,773,794 B2 | 8/2010 | Russakoff | |
| 7,796,795 B2 | 9/2010 | Uppaluri | |
| 8,634,625 B2* | 1/2014 | Flohr | G06T 5/50 382/128 |
| 2002/0126879 A1* | 9/2002 | Mihara | G06K 9/00201 382/118 |
| 2004/0101104 A1* | 5/2004 | Avinash | A61B 6/032 378/98.12 |
| 2005/0191620 A1* | 9/2005 | McDevitt | C12Q 1/6816 435/5 |
| 2005/0280828 A1* | 12/2005 | Fitzgerald de Boer | G01B 9/02091 356/497 |
| 2006/0013482 A1* | 1/2006 | Dawant | G06T 7/149 382/173 |
| 2006/0109949 A1* | 5/2006 | Tkaczyk | A61B 6/032 378/4 |
| 2009/0022394 A1* | 1/2009 | Banerjee | G06F 3/04845 382/164 |
| 2010/0111396 A1* | 5/2010 | Boucheron | G06K 9/0014 382/133 |
| 2010/0128948 A1* | 5/2010 | Thomsen | A61B 6/032 382/131 |
| 2010/0215230 A1* | 8/2010 | Bornefalk | G06T 11/005 382/128 |
| 2012/0238870 A1* | 9/2012 | Smith | A61B 6/025 600/431 |
| 2014/0219534 A1* | 8/2014 | Wiemker | G06T 7/0012 382/131 |
| 2016/0019432 A1* | 1/2016 | Fredenberg | A61B 6/482 382/131 |

OTHER PUBLICATIONS

Cahn, R. N., et al.; Detective quantum efficiency dependence on x-ray energy weighting in mammography; 1999; Med. Phys.; 26(12)2680-2683.

Cardinal, H. N., et al.; An accurate method for direct dual-energy calibration and decomposition; 1990; Med. Phys.; 17:327.

Fredenberg, E., et al.; Optimization of mammography with respect to anatomical noise; 2011; Proc. SPIE: Medical Imaging; 796112.

Norell, B., et al.; Lesion characterization using spectral mammography; 2012; Proc. of SPIE: Medical Imaging; 8313.

Santamaria-Pang, A., et al.; Automated Liver Lesion Characterization using fast kVp switching Dual Energy Computed Tomography Imaging; 2010; Proc. of SPIE: Medical Imaging; 7624.

Wang, A. S., et al.; Synthetic CT: Simulating low dose single and dual energy protocols from a dual energy scan; 2011; Med. Phys.; 38(10)1-10.

\* cited by examiner

METHOD AND X-RAY SYSTEM FOR COMPUTER AIDED DETECTION OF STRUCTURES IN X-RAY IMAGES

CROSS REFERENCE TO RELATED APPLICATIONS

This application is a national filing of PCT application Ser. No. PCT/IB2014/059122, filed Feb. 20, 2014, published as WO 2014/147495 A2 on Sep. 25, 2014, which claims the benefit of U.S. provisional application Ser. No. 61/803,906 filed Mar. 21, 2013, which is incorporated herein by reference.

FIELD OF THE INVENTION

The present invention relates to X-ray imaging technology as well as image post-processing. In particular, the present invention relates to a method and an X-ray system for computer aided detection of structures in X-ray images, a computer-readable medium, a program element, a processing element as well as the use of a method for computer aided detection.

Particularly, the present invention relates to detecting structures in X-ray images by evaluating spectral information within the X-ray image.

BACKGROUND OF THE INVENTION

Computer aided detection of tissue structures of interest is becoming increasingly important in radiology, in particular in mammography. Computer aided detection corresponds to a technique that detects suspicious regions within an acquired X-ray image by comparing visible feature shapes to a reference library. In general, spatial information, i.e. feature shape, is evaluated without respect to absolute values in the image, i.e. a signal strength. In particular in mammograms, the occurrence of anatomical noise is limiting the ability to detect lesions. Contrast from both anatomical noise and suspicious lesions decrease with photon energy and, depending on the lesion type, its visibility may be optimized at a certain photon energy. E.g., tumor detectability is improved at higher energies while micro-calcifications may preferably be detected at lower energies. In particular, tumors are heavily affected by anatomical noise and the decrease in anatomical noise at higher energies outweighs the decrease in tumor contrast, whereas microcalcifications are less affected by anatomical noise and reducing the amount of anatomical noise has little impact.

Accordingly, employing image information, which is acquired at a specific photon energy is referred to as spectral imaging or employing spectral information. The energy E of a single photon is inversely related to its wavelength λ by the formula $$E = \frac{h*c}{\lambda}$$

(with E: energy, h: Planck's constant, c: speed of light).

Spectral imaging employs the detected energy spectrum to extract information about the material contents of the object. The technique has the potential to improve detection also at screening without contrast agent, i.e. unenhanced imaging, which however may increase the amount of quantum noise present in image information.

B. Norell, E. Fredenberg, K. Leifland, M. Lundqvist, B. Cederström, "Lesion characterization using spectral mammography" SPIE Medical Imaging 2012: Physics of Medical Imaging describes using spectral image information for characterizing and distinguishing detected structures in an X-ray image.

SUMMARY OF THE INVENTION

One object of the present invention may be seen as providing an improved computer aided detection of structures in an X-ray image. This object is achieved by the subject-matter of the independent claims. Preferred embodiments of the present invention are described in the dependent claims.

The present invention employs spectral image information for detecting and characterizing structures in an X-ray image. In particular, X-ray image information relating to a specific energy or having a specific energy weighting may be employed with the energy or energy weighting being chosen such that a certain type of tissue, in particular its visibility within the X-ray image information, is either optimized or minimized. Subsequently, a computer aided detection algorithm is employed, which also considers the spectral information or energy information of the X-ray image information. In other words, for example, a certain type of tissue structure or lesion may have an optimal visibility (e.g. high contrast or signal-to-noise ratio) in an X-ray image employing a first defined energy, while the same structure has a minimal visibility (low contrast or signal-to-noise ratio) in image information having a further energy.

Consequently, a computer aided detection (CAD) algorithm may employ knowledge that a certain type of tissue, e.g. a tumor, has a preferred visibility at one energy, while having a minimized visibility at another energy. The algorithm may thus employ said knowledge to determine the type of tissue structure within the image information when evaluating the X-ray images. In case a further X-ray image is determined relating to a specific energy, the CAD algorithm may detect structures in said image information and subsequently determines, which type of tissue is optimally visible at this specific energy. The CAD algorithm may subsequently synthesize a further X-ray image having a different energy for which the algorithm knows that a certain (previously detected) type of tissue has minimal visibility. By analyzing the further X-ray image, the determination whether a characterization of a tissue structure is correct may be verified.

With spectral imaging methods, the energy dependence of an imaged material's attenuation may be extracted. In particular, when using at least two images corresponding to different X-ray energies, further X-ray images may be determined having a specific energy signature. In other words, from two different X-ray energy images, a further X-ray image may be synthesized or computed corresponding to an X-ray image as it would appear at any given energy of mono-energetic photons. Computer aided detection of specific features may be optimized by synthesizing images at certain energies that are optimal for the detection of a respective feature and then use a computer aided detection algorithm on accordingly optimized image information.

Aspects, features and advantages of the present invention may further be derived from the detailed description of preferred embodiments described hereinafter, which are explained with reference to the following drawings. Like elements are referred to with like reference numerals. The figures are not drawn to scale, however may depict qualitative proportions.

DETAILED DESCRIPTION OF PREFERRED EMBODIMENTS

Both common computer aided detection and unenhanced spectral imaging suffer from poor specificity and/or poor sensitivity. Thus, the use of spectral methods to optimize an X-ray image for computer aided detection of different features before the actual detection algorithm is processing the image information is proposed. By comparing the relative detection at different energies, tissue may be characterized and thereby specificity may be increased. In other words, it is proposed to combine traditional computer aided detection, which evaluates spatial information and target shape, with spectral imaging, which extracts absolute information about the signal strength and may evaluate the target material.

Figure 1A:
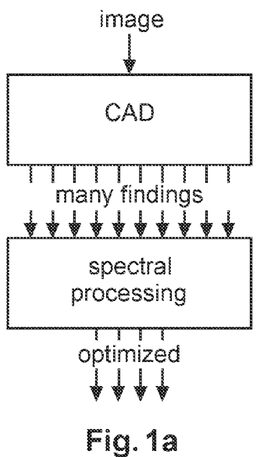
FIGS. 1a-c show three exemplary implementations of the present
invention.
Figure 1B:
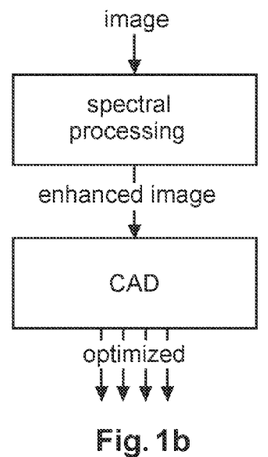
Figure 1C:
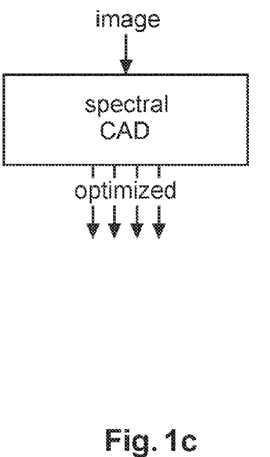

FIGS. 1a-c depict three exemplary implementations of the present invention. One implementation of the invention according to FIG. 1a is to employ a computer aided detection algorithm for determining image structures in X-ray image information as input, which compares detected image structures with a library of features. Subsequently, a spectral processing algorithm employs a spectral library or look-up table for different target materials, which considers as input a spectral X-ray image and possibly background references, in the field of mammography e.g. information as to breast glandularity and thickness, which is measured in a region outside the finding.

In other words, the standard CAD system is applied to extract suspicious features from the summed image in a spectral X-ray image, in particular a spectral mammogram, as the sum of the energy resolved images. The summed image may be identical to a conventional X-ray image or mammogram using a regular CAD system. The specificity may typically be poor with a large number of findings being returned for each image. The CAD system may thus supply the found regions of interest of the respective tissue structures of interest to a spectral processing program. The latter may e.g. grow a reference region around each feature that has been detected. Spectral material decomposition may be applied to extract background information from the reference region, e.g. breast glandularity and thickness. Material decomposition is subsequently applied to the suspicious findings itself, with the background information as additional input. A confidence measure to increase specificity may be returned, for instance the likelihood for the finding to be benign or malignant. The confidence measure may be appropriately thresholded to extract the most suspicious findings.

A further implementation of the invention is shown in FIG. 1b, where CAD and spectral processing are performed in reversed order, so that the spectral processing optimizes the image for performance of the CAD algorithm. One example is to apply the CAD system on a synthesized image with optimal energy. Another example is to apply the CAD algorithm on a material decomposed image. E.g., if material decomposition or synthesized image energy is employed to reduce the amount of anatomical noise, e.g. overlapping tissue, the CAD system may improve specificity. Modifications to a common CAD system may be employed to counteract increased noise.

A further implementation of the present invention according to FIG. 1c is to completely integrate and merge material decomposition with a computer aided detection algorithm into a single system resulting in spectral properties being part of the CAD library. Hence, a merged spectral-processing and computer aided detection algorithm with image structures and a spectral X-ray image as input may be employed using a library consisting of both spatial and spectral feature information.

When it is referred to that the computer aided detection algorithm is adapted to evaluate spectral information of the X-ray image for detecting the tissue structure of interest in the context of this patent application, each exemplary implementation according to one of FIGS. 1a to c shall be included. In particular, the computer aided detection algorithm may perform a spectral processing and/or evaluation of the X-ray image after evaluating the X-ray image for tissue structure shape, alternatively the computer aided detection algorithm may perform a spectral processing and/or evaluation of the X-ray image prior to evaluating the X-ray image for tissue structure shape or the computer aided detection algorithm may perform a spectral processing and/or evaluation of the X-ray image concurrently to evaluating the X-ray image for tissue structure shape, e.g. by employing a spectral CAD library or database.

Preferably, the X-ray image information consists of at least two individual images that have been acquired at different X-ray energies. A special case of the present invention, particularly referring to the case in FIG. 1a, is lesion characterization using a lesion characterization tool being applied manually by the radiologist to retrieve more information about a suspicious circular or oval finding, in particular in mammography applications. Such findings could either be benign cysts or malignant tumors determined after a patient has left, and may often lead to recalls of the patient, which may cause stress and may be costly.

Using the lesion characterization, the radiologist may mark a lesion or tissue structure of interest in an X-ray image and a reference region is grown around the tissue structure of interest. The reference region may provide additional information to material decomposition of the lesion itself and the radiologist is provided with glandularity, thickness and a confidence measure for whether the lesion is likely to be benign or malignant.

In accordance with the inventive concept of the present patent application, an automated lesion characterization may be employed, in which the CAD system instead of a radiologist detects the cyst/tumor. The spectral CAD system may, analogous to the lesion characterization tool, also provide breast glandularity, thickness and a confidence measure to the radiologist for each finding that has been determined by the spectral CAD algorithm.

Round or oval lesions are relatively easy to detect in X-ray image information but are often difficult to be characterized as benign cysts or malignant tumors. A characterization of a lesion or a tissue structure of interest into tumor or a cyst already at screening is a particular advantage of spectral X-ray systems as slight differences in the attenuation between cysts and tumors can be traced by comparing the spectral signals encoded in high energy measurements and low energy measurements, e.g. two X-ray images using different X-ray energies.

Again a region of interest/a lesion region and a reference region are compared. Variations in the glandularity of the breast tissue, e.g. in mammography applications, for a lesion region and a reference region, but also lesion shape, spiculations and paddle tilt or the location of the lesion close to the boundary of the breast all lead to an erroneous identification of potentially malignant tumors as benign cysts (false negatives) and cysts as tumors (false positives).

For a preferred determination and classification and thus reducing an erroneous identification of cysts or tumors, also a tilt of the compression paddle during the examination in a mammogram may be considered. The subsequently described method may also be applied to peripheral regions where the height of breast tissue examined is a fast changing function of the lateral spatial coordinate of the detector. Thereby, adverse effects of compression paddle tilt may be effectively eliminated.

Again with regard to a lesion characterization tool, a likelihood ratio is employed to verify or falsify the hypotheses of the malignancy of a lesion or a detected tissue structure of interest. Regions of interest in and around the lesion are defined and the corresponding averages within the region of interest are used for the characterization. Therefore, it is regularly assumed that the compressed breast height is constant over the entirety of the reference region of interest and the lesion region of interest. If that assumption is false, the receiver operating characteristic (ROC) curves summarizing the possible choices for sensitivity and specificity, depending on decision threshold, degrades quickly. Accordingly, it is proposed to adapt the model for the lesion within the region of interest such that a linear gradient in thickness is assumed for both regions of interest (reference region and lesion region of interest) and fitted during the likelihood estimation for the two additional fit parameters, one for each direction of a two-dimensional image.

A linear gradient assumption may be sufficient for many situations, where the lesion is well inside the breast, where the changes in compressed thickness over the region of interest are small. However, in case peripheral regions are examined, linear gradients may not be sufficient, which would result in the method of the present invention to be generalized to fit a quadratic surface with three additional parameters or even a higher order surface.

Figure 2A:
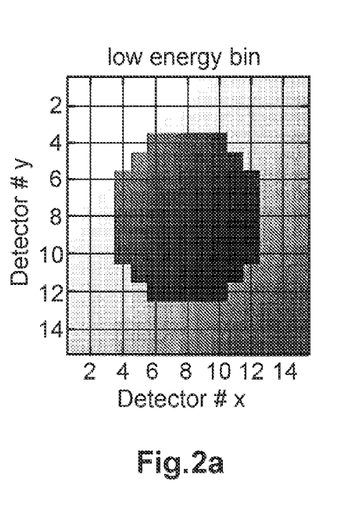
FIGS. 2a,b show simulated low energy and a high energy bin measurement results of a spherical lesion according to the present invention.
Figure 2B:
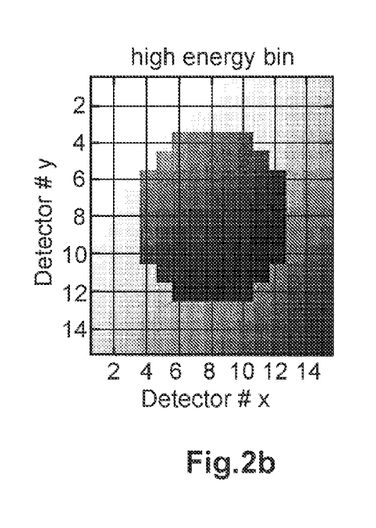

FIGS. 2a and 2b show a low energy bin image (FIG. 2a) and a high energy bin image (FIG. 2b) of a breast lesion of 10 mm diameter embedded in a bulk of 50 mm breast tissue with average height of 50 mm. The influence of paddle tilt is visible in both images seen by the gradient in intensities. The assumed gradients in this example are 0.3 mm of change in height for each 1 mm progression in any direction of the two image directions.

Thus, FIGS. 2a,b show simulated measurement results of a spherical lesion of 10 mm diameter embedded in breast tissue of 50 mm height. The scan parameters exemplarily are 32 kVp with a two bin photon counting detector with energy thresholds at around 10 keV and 22 keV. FIG. 2a shows the low energy bin, FIG. 2b the high energy bin.

Pixel binning is employed to 1 mm×1 mm. Both FIGS. 2a,b show the effect of a thickness gradient due to a tilt of the surface of the breast support with respect to the surface of the compression paddle, causing a linear change in height in both image directions by 0.3 mm per mm progression. This leads to a left to right and bottom to top difference in thickness of the compressed tissue by 4.5 mm in both directions, shown by the increase in darkness.

To compensate for this difference in tissue thickness, the present invention proposes to determine the ray likelihood for each pixel with coordinates i,j in the lesion region of interest with yy being the measurement value in any of the two energy bins, $t_{ij}$ characterizing a model for the lesion shape and h, g being the average compression height and the average glandularity in the entire region.

Regularly, neither the compression height nor the average glandularity will in practice be constant over the lesion region of interest and the reference region of interest. Rather, both are functions of the spatial coordinates. The likelihood is determined by equation 1.

$$L_{ij}(h, g, t_{ij}(t_1, t_2, t_3, \alpha)|y_{ij}) \quad \text{Equation 1}$$

Considering equation 1, modeling for linear deviations from the assumption of constant height results in equation 2.

$$L_{ij}(h_{ij}(h_0, g_x, g_y), g, t_{ij}(t_1, t_2, t_3, \alpha)|y_{ij}) \quad \text{Equation 2}$$

In the simplest case with linear gradients, the height deviation may be modeled in accordance with equation 3.

$$h_{ij}(h_0, g_x, g_y) = h_0 + ig_x + jg_y \quad \text{Equation 3}$$

In case of curved breast shapes at peripheral areas, equation 3 could be altered to include additional terms.

The same model with regard to height gradients (equation 3) must be used for the reference region of interest to make sure the assumption of a continuous change in breast shape is respected.

FIGS. 4a show the histograms for tumors (left histogram) and cysts (right histogram) for the case where gradients are present in the object of interest and are assumed to be known in the likelihood estimation for the assumptions that a lesion corresponds to a cyst and a lesion corresponds to a tumor. FIG. 3b shows the same case where gradients are present but are neglected during the likelihood estimation. FIG. 3c shows the case where the likelihood allows for gradients as two additional estimation parameters. Comparing FIG. 3a to 3c, the bias introduced by the negligence of the gradients (FIG. 3b) is substantially completely removed by the extension of the model to fit the gradients as well.

Figure 3A:
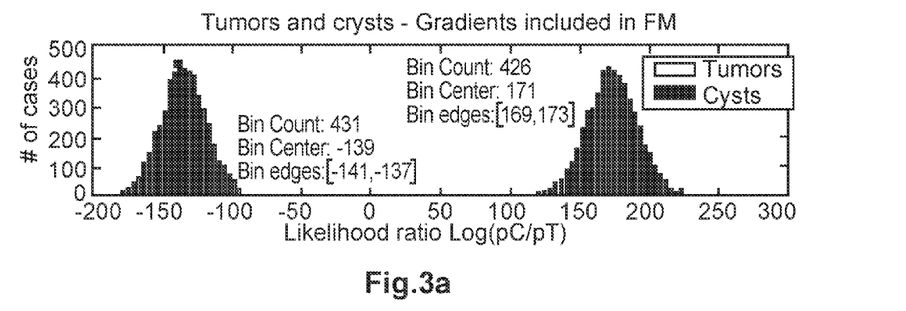
FIGS. 3a-c show exemplary histograms for tumors and cysts according to the present invention.
Figure 3B:
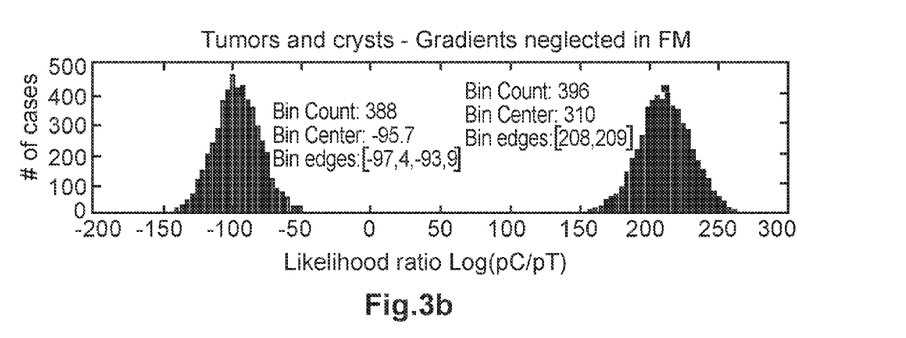
Figure 3C:
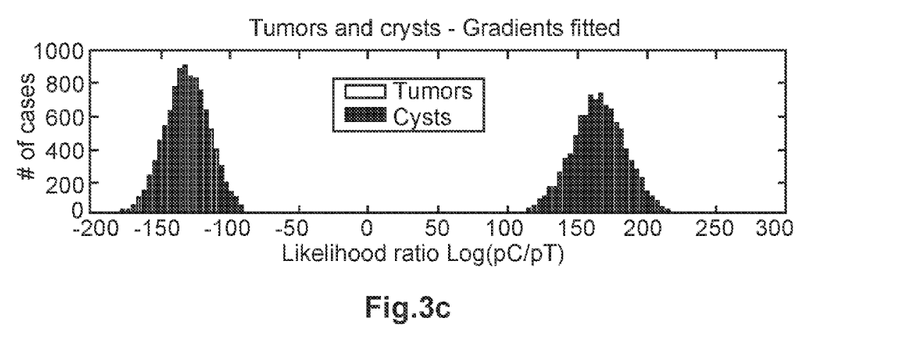

FIGS. 3a-c thus demonstrate the influence of the correct and wrong assumptions regarding thickness gradients present in an object of interest. FIG. 3a shows the case of a known thickness gradient (which assumption in practice is not regularly known), the histograms of 5000 tumors (left histogram) and cysts (right histogram) are very well separated for rather high values of radiation dose and all cases are identified correctly. For the cases where a gradient, caused e.g. by paddle tilt, is present (FIG. 3b), a shift of both histograms is noticeable, which at a realistic dose level increases the number of tumors identified as cysts, because the tumor histogram moves closer to the decision threshold "0". This shift is entirely due to the systematic influence of the unknown paddle tilt (e.g. 0.3 mm/mm progression in both directions). FIG. 3c shows how the correction of the method according to the present invention, where the gradients in both directions are fitted during the likelihood estimation with equations 2 and 3 are employed, remove the influence of the gradients. In particular, the centers of the histograms are substantially back at the correct position as if the gradients in the two heights were known exactly (FIG. 3c versus FIG. 3a).

Similar to a gradient with regard to height, glandularity variations may be taken into account, e.g. by means of a slowly varying function of a position, which describes the spatial variations of glandularity g(x,y) in accordance with equation 4.

$$L_{ij}(h_{ij}(h_0, g_x, g_y), g(x, y), t_{ij}(t_1, t_2, t_3, \alpha)|y_{ij}) \quad \text{Equation 4}$$

In another embodiment, variations of thickness and/or glandularity in the reference region may be used to model the respective quantities in the lesion region. Further, gradients which are relatively large could be penalized or considered to be very unlikely. Further, different larger gradients could be accepted in a peripheral region than in a central compressed region.

Equation 3 describes an essentially flat geometry where the only deviation from a planar compression is by means of a slight deviation from parallel of the compression paddle and the breast support. However, in a particular mammography system, neither the breast support nor the compression paddle may be planar but rather curved by design. Thus, depending on compression height, the breast height will be a more complicated function of detector position, but may still be modeled accurately considering the geometric properties of the respective mammography systems.

Deviations from the design height map h(x,y) of a particular mammography system may similarly be detected and fitted in accordance with the method described previously.

A further example for a computer aided detection that would benefit from spectral processing is the classification of micro-calcifications. Regularly, two chemically different types of calcifications are known, type 1 calcification (calcium oxalate dehydrate) and type 2 calcification (calcium hydoxyapatite). Regularly, only type 2 micro-calcifications go along with malignant tumors. Therefore, using a computer aided detection algorithm which also determines, which type of calcification is present in a tissue, may be highly beneficial to distinguish between tumors and cysts for improved diagnosis. A spectral acquisition and appropriate CAD algorithms provide sufficient information to distinguish between the two types of calcifications.

Further, the known energy-dependent weighting of the at least one X-ray image for which the visibility of a certain tissue structure shape is optimized or minimized may be employed when characterizing a tissue type.

For implementing the present invention, particularly referring to the case in FIG. 1b, an algorithm for synthesizing a set of images is employed, wherein each synthesized image corresponds to a specific X-ray energy that optimizes detection for some specific features or tissue structure shapes. Such a synthesized image may correspond to a substantially mono-energetic image or may comprise an energy-dependent weighting. A mono-energetic X-ray image may comprise only image information provided by detecting photons having a specific energy, though minor deviations from a precise energy value may be allowable. A mono-energetic X-ray image may thus comprise an energy-dependent weighting with only a specific energy value.

In case a certain bandwidth around a specific energy value is allowed, such would result in an energy-dependent weighting corresponding to a bandpass. Similar to analogue filters, the energy-dependent weighting may thus comprise a lowpass structure, a highpass structure, a bandpass structure or a notch structure. Even an arbitrary combination of structures may be conceivable. E.g. in case a tissue type has a preferred visibility around two independent, separate energy values, a synthesized X-ray image could thus employ an energy-dependent weighting consisting of two separate mono-energetic energy values or two separate bandpass structures in combination.

A computer aided detection algorithm may subsequently evaluate the spectral information, i.e. the energy information, of the energy-dependent weighting of the X-ray image, when detecting a tissue structure of interest. In case a plurality of synthesized X-ray images is provided, a computer aided detection algorithm may sequentially go through the different synthesized images and evaluate each image under consideration of its spectral information for visible or also a lack of visibility of a certain structure. E.g., an "optimal" visibility of a certain tissue structure in one X-ray image having a first energy weighting and a subsequent "minimized" visibility of the same tissue structure in a further X-ray image having a different energy weighting or energy value may allow determining the tissue type and thus may allow characterization of the tissue structure of interest, in particular not only considering the shape of the structure, that is visible (or not visible) in the X-ray images but also further employing the information regarding the energy value of the (synthesized) X-ray image.

The same or a further algorithm may also check for consistency and may compare differences in the findings from different images for analyzing tissue structures of interest.

A further aspect may be using an algorithm, the same or a further, that automatically identifies at least one synthesized image out of a plurality of synthesized images, which yields optimal computer aided detection results for a certain imaging task, e.g. with regard to a specific tissue structure of interest.

With two (or more) samples of material attenuation from the energy images, the relative amount of photoelectric effect and Compton scatter may be estimated and the full attenuation versus energy may be reconstructed. It is thus possible to synthesize images corresponding to mono-energetic photons of an arbitrary photon energy e.g. within the range relevant for mammography or for any photon energies combined into an arbitrary energy spectrum, i.e. having an arbitrary energy-dependent weighting.

Regularly, a material separation is computed from a high and a low energy X-ray into two base materials such as aluminum (Al) and polymethyl methacrylate (PMMA) or e.g. adipose and glandular tissue. Using computed material decomposition as known in the art and the known X-ray attenuation of the base materials over the relevant energy range, a synthesized X-ray image $I_{syn}$ may be computed for each single energy E and more generally for each arbitrary X-ray spectrum $I_0(E)$ and energy-dependent weighting $w(E)$ by using equation 5.

$$I_{syn} = \int_0^\infty w(E) I_0(E) e^{-\mu_a(E) t_a - \mu_g(E) t_g} dE \quad \text{Equation 5}$$

with energy-dependent weights $w(E)$ and attenuation functions $\mu_A(E)$, $\mu_G(E)$ of the material separation ($t_a$, $t_b$) of the base materials.

Figure 4A:
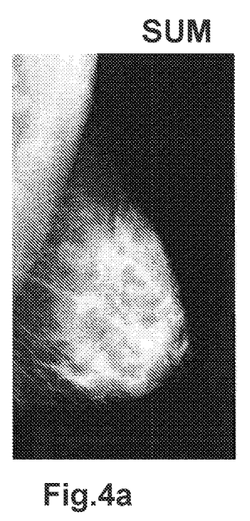
FIGS. 4a-c show exemplary illustrations of mammograms.
Figure 4B:
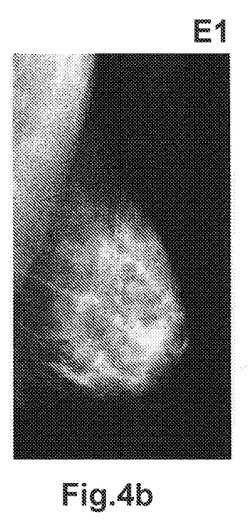
Figure 4C:
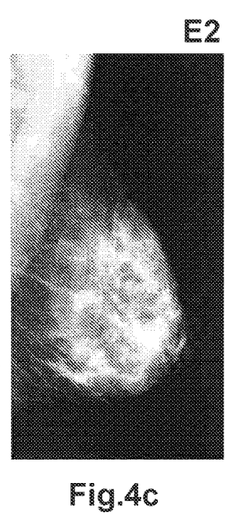

FIGS. 4a-c show an exemplary illustration of a conventional mammogram (FIG. 4a —some of high and low energy mammogram) as well as two virtually mono-energetic computed mammograms at different energies $E_1$ and $E_2$ (FIG. 4b,c).

As may be taken from FIGS. 4a-c, by generating a set of images that correspond to energies, which optimize or minimize the detectability of different features, the output of a computer aided detection algorithm, thus a CAD analysis of these images, may be enhanced or optimized. As the optimal energies depend on the power spectrum of the anatomical noise and such a spectrum may be derived by spectral techniques, such may be employed in a spectral CAD algorithm.

Further, for specific findings, i.e. the identification of specific tissue structures of interest, the CAD output for the different energies may typically determine at least one X-ray image that optimizes (the visibility) and at least one X-ray image that (presumably) minimizes (the visibility) of the feature or the tissue structure of interest, which may be compared, in particular under consideration of the respective energy of the X-ray image, and may provide additional information about the feature. In other words, an image feature or tissue structure of interest that is matched to a feature in the CAD library (a visually detected feature within the X-ray image is assumed to correspond to a certain feature in the library) may thus be predicted to be enhanced (having optimal visibility) at some energy while being minimized (its visibility) at a further energy. This information may then be employed for a check for consistency, whether the match of the detected feature with the corresponding library feature is accurate, thereby increasing specificity.

In a further embodiment, the mono-energetic X-ray images may be computed for a complete range of relevant energies and the best result of the computer aided detection algorithm is selected automatically, e.g. by maximizing a goodness value of the current CAD task. In other words, a plurality of synthesized X-ray images are computed, the computer aided detection algorithm is subsequently employed with regard to each synthesized X-ray image and the outcome (i.e. the determination of a certain feature or characterization of tissue structure of interest) employing a certainty indicator, with that CAD result is presented, which is identified to comprise the most accurate result.

The goodness value may be seen as a target function to be optimized over a selected energy range, which is chosen dependent on the CAD task under consideration. In a segmentation task, for example, the goodness value may be chosen as the average gradient along the resulting segmentation contour of the CAD algorithm. Hence, the goodness value is maximal for the segmentation with the strongest average gradient along its contour, which defines the best visibility of the structure under investigation in this example.

In this way, the optimal energy for a specific tissue structure of interest is automatically selected and subsequently the corresponding virtually mono-energetic X-ray image may be displayed together with the computer aided detection overlay. Thus, that energy corresponding to the detection that is considered to be most accurate is automatically selected.

The present invention thus relies on the availability of at least two X-ray images corresponding to different X-ray energies. Such images may be acquired subsequently using different X-ray energies or, preferably, may be provided by a spectral photon counting system, which may be able to deliver spectral information from a single exposure, thus without increasing radiation dose to a patient or affecting workflow.

Figure 5:
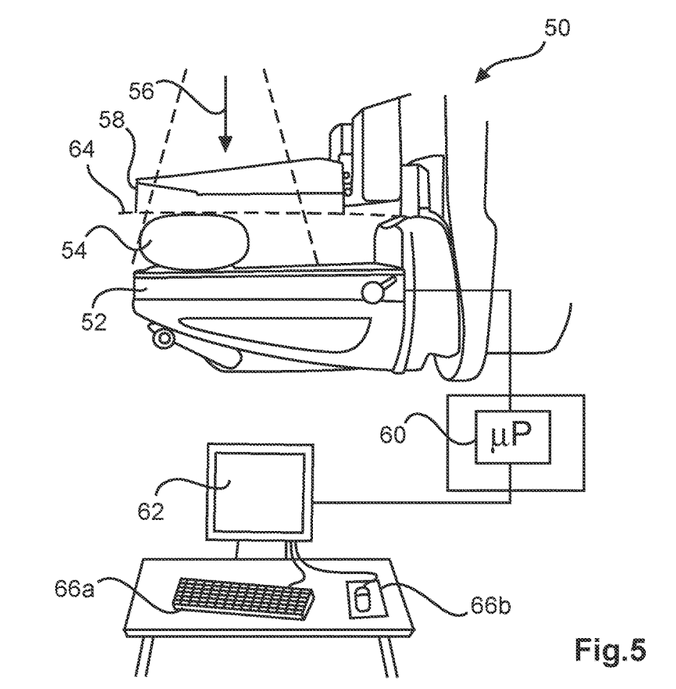
FIG. 5 shows an exemplary X-ray system according to the present invention.

Now referring to FIG. 5, an exemplary embodiment of a mammography system employing the method according to the present invention is depicted.

Mammography system 50 employs a detector 52 as well as a compression paddle 58 between both of which an object of interest 54 is situated. X-radiation 56 may be introduced for acquiring X-ray information of the inner structure of the object of interest 54. The relative orientation of the detector 52 and the compression paddle 58 may comprise a slight deviation from a fully parallel orientation or in other words a tilt 64, resulting in a variation in height of the object 54. X-ray information, e.g. in the case of a digital mammography system, may be provided to microprocessor 60, which may also be arranged to execute a computer program for controlling X-ray system 50 as well as executing the method 70 for computer aided detection of structures in X-ray images according to the present invention. A computer-readable medium may be provided on which a computer program adapted to perform the method according to the present invention is stored as well as a program element may be provided to the processor 60 which is adapted, when being executed to control an X-ray system 60 and particular to perform the method according to the present invention.

The result of a spectral computer aided detection algorithm may be presented to an operator or radiologist using display 62. Operation of the method according to the present invention as well as X-ray system 50 may be controlled by input devices 66a,b.

Figure 6A:
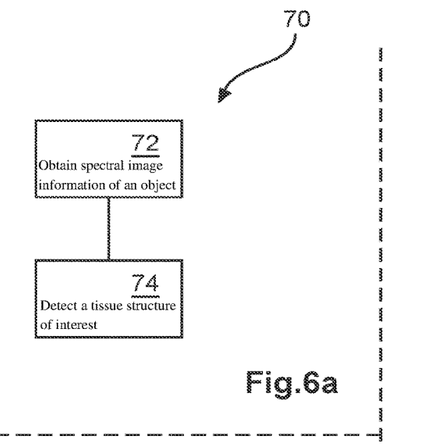
FIGS. 6a-c show exemplary embodiments of the method for computer aided detection of structures in X-ray images according to the present invention.

FIG. 6a shows a method 70 for computer aided detection of structures in X-ray images comprising the steps of obtaining 72 spectral image information of an object, and detecting 74 a tissue structure of interest in the X-ray image by employing a computer aided detection algorithm, which may in particular be adapted to evaluate spectral information of the X-ray image.

Figure 6B:
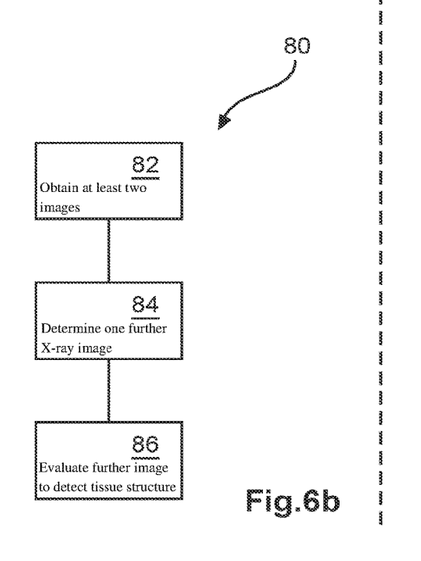

According to FIG. 6b, method 70 may be embodied as method 80 further comprising obtaining 82 at least two X-ray images corresponding to at least two different X-ray energies, determining 84 from the at least two X-ray images at least one further X-ray image, wherein the at least one further X-ray image is an X-ray image having a defined energy-dependent weighting, in particular different from the X-ray energies of the at least two X-ray images, and evaluating 86 the at least one further X-ray image for detecting a tissue structure shape of a tissue structure of interest. Determining 84 the at least one further X-ray image may in particular be performed by computing the at least one further X-ray image, e.g. by employing the equation 5.

Figure 6C:
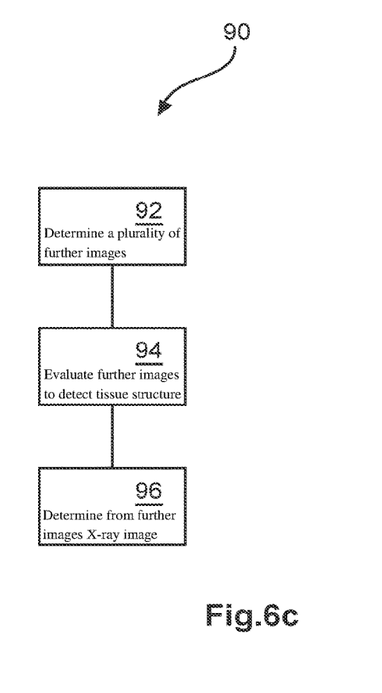

According to FIG. 6c, method 70 according to the present invention may be embodied as a method 90 further comprising determining 92 a plurality of further X-ray images, each further X-ray image having a defined individual energy-dependent weighting, evaluating 94 the plurality of further X-ray images for detecting the tissue structure shape and determining 96 from the plurality of further X-ray images at least one X-ray image by optimizing or minimizing visibility of a certain tissue structure shape.

The so determined X-ray image having the optimized or minimized visibility of a certain tissue structure shape may subsequently be presented to an operator of the X-ray system.

LIST OF REFERENCE SIGNS

50 X-ray system
52 X-ray detector
54 object
56 X-radiation
58 compression paddle
60 microprocessor
62 display
64 paddle tilt
66a,b input devices 70 method for computer aided detection of structures
72 obtaining spectral image information
74 detecting a tissue structure of interest
80 method for computer aided detection of structures
82 obtaining at least two X-ray images
84 determining at least one further X-ray image
86 evaluating the at least one further X-ray image
90 method for computer aided detection of structures
92 determining a plurality of further X-ray images
94 evaluating the plurality of further X-ray images
96 determining at least one further X-ray image

The invention claimed is:

1. A method for computer aided detection of a tissue structure in X-ray images, the method comprising:
obtaining spectral X-ray image information of an object;
wherein the spectral X-ray image information constitutes at least one X-ray image; and
detecting a tissue structure of interest in the X-ray image by employing a computer aided detection algorithm;
wherein detecting a tissue structure of interest in the X-ray image comprises the computer aided detection algorithm being adapted to evaluate the X-ray image for tissue structure shape and compare the tissue structure shape with a plurality of pre-determined tissue structure shapes; and
wherein the computer aided detection algorithm is adapted to evaluate spectral information of the X-ray image for detecting the tissue structure of interest;
wherein the method further comprises: obtaining at least two X-ray images corresponding to at least two different X-ray energies;
determining from the at least two X-ray images at least one further X-ray image, which corresponds to the X-ray image of the spectral X-ray information;
wherein the at least one further X-ray image is an X-ray image having a defined energy-dependent weighting, wherein the energy-dependent weighting causes the further X-ray image to correspond to photon energies which are combined into an energy spectrum; and
wherein the method further comprises evaluating the at least one further X-ray image for detecting the tissue structure shape;
wherein the determining of the at least one further X-ray image employs equation $$I_{syn} = \int_0^\infty w(E) \, I_0(E) e^{-\mu_a(E) t_a - \mu_g(E) t_g} dE;$$

wherein w(E) represent energy-dependent weights of the energy-dependent weighting, $\mu_A(E)$, $\mu_G(E)$ represent attenuation functions of two materials, $t_a$ and $t_b$ represent a material separation of the two materials and $I_0(E)$ represents an X-ray spectrum.

2. The method according to claim 1, further comprising determining a plurality of further X-ray images, each further X-ray image having an individual defined energy-dependent weighting; and
evaluating the plurality of further X-ray images for detecting the tissue structure shape; and
determining from the plurality of further X-ray images at least one X-ray image by optimizing or minimizing visibility for a certain tissue structure shape.

3. The method according to claim 2, wherein determining from the plurality of further X-ray images at least one X-ray image by optimizing or minimizing visibility for a certain tissue structure shape comprises determining an associated energy-dependent weighting applied to the at least one X-ray image.

4. The method according to claim 3, wherein the determined associated energy-dependent weighting is employed for detecting the tissue structure of interest, in particular by employing an energy-dependent visibility of a certain tissue structure of interest.

5. The method according to claim 1, wherein the computer aided detection comprises one of performing first a computer aided detection algorithm and second a spectral evaluation on an X-ray image, performing first a spectral evaluation and second a computer aided detection algorithm on an X-ray image, and performing a combined spectral computer aided detection algorithm on an X-ray image.

6. An X-ray system for detecting a tissue structure, comprising:
at least one electronic processor programmed for:
obtaining spectral X-ray image information of an object;
wherein the spectral X-ray image information constitutes at least one X-ray image; and
detecting a tissue structure of interest in the X-ray image by employing a computer aided detection algorithm;
wherein detecting a tissue structure of interest in the X-ray image comprises the computer aided detection algorithm being adapted to evaluate the X-ray image for tissue structure shape and compare the tissue structure shape with a plurality of pre-determined tissue structure shapes; and
wherein the computer aided detection algorithm is adapted to evaluate spectral information of the X-ray image for detecting the tissue structure of interest;
wherein the method further comprises: obtaining at least two X-ray images corresponding to at least two different X-ray energies;
determining from the at least two X-ray images at least one further X-ray image, which corresponds to the X-ray image of the spectral X-ray information;
wherein the at least one further X-ray image is an X-ray image having a defined energy-dependent weighting, wherein the energy-dependent weighting causes the further X-ray image to correspond to photon energies which are combined into an energy spectrum; and
wherein the method further comprises evaluating the at least one further X-ray image for detecting the tissue structure shape;
wherein the determining of the at least one further X-ray image employs equation $$I_{syn} = \int_0^\infty w(E) \, I_0(E) e^{-\mu_a(E) \, a - \mu_g(E) t_g} dE;$$

wherein w(E) represent energy-dependent weights of the energy-dependent weighting, $\mu_A(E)$, $\mu_G(E)$ represent attenuation functions of two materials, $t_a$ and $t_b$ represent a material separation of the two materials and $I_0(E)$ represents an X-ray spectrum.

7. The X-ray system according to claim 6, being adapted as a spectral photon counting system.

8. A non-transitory computer-readable medium comprising a stored computer program adapted to perform a method for computer aided detection of a tissue structure in X-ray images, the method comprising:
obtaining spectral X-ray image information of an object;
wherein the spectral X-ray image information constitutes at least one X-ray image; and
detecting a tissue structure of interest in the X-ray image by employing a computer aided detection algorithm;
wherein detecting a tissue structure of interest in the X-ray image comprises the computer aided detection algorithm being adapted to evaluate the X-ray image for tissue structure shape and compare the tissue structure shape with a plurality of pre-determined tissue structure shapes; and wherein the computer aided detection algorithm is adapted to evaluate spectral information of the X-ray image for detecting the tissue structure of interest;

wherein the method further comprises; obtaining at least two X-ray images corresponding to at least two different X-ray energies;

determining from the at least two X-ray images at least one further X-ray image, which corresponds to the X-ray image of the spectral X-ray information;

wherein the at least one further X-ray image is an X-ray image having a defined energy-dependent weighting, wherein the energy-dependent weighting causes the further X-ray image to correspond to photon energies which are combined into an energy spectrum; and wherein the method further comprises evaluating the at least one further X-ray image for detecting the tissue structure shape;

wherein the determining of the at least one further X-ray image employs equation $$I_{syn} = \int_0^\infty w(E) I_0(E) e^{-\mu_a(E) t_a 31} \mu_g(E) t_g dE;$$

wherein w(E) represent energy-dependent weights of the energy-dependent weighting, $\mu_A(E)$, $\mu_G(E)$ represent attenuation functions of two materials, $t_a$ and $t_b$ represent a material separation of the two materials and $l_0(E)$ represents an X-ray spectrum.

9. The X-ray system according to claim 6, wherein the at least one electronic processor is further programmed to:
   determine a plurality of further X-ray images, each further X-ray image having an individual defined energy-dependent weighting;
   evaluate the plurality of further X-ray images for detecting the tissue structure shape; and
   determine from the plurality of further X-ray images at least one X-ray image by optimizing or minimizing visibility for a certain tissue structure shape.

10. The X-ray system according to claim 9, wherein the at least one electronic processor is further programmed to:
    determine an associated energy-dependent weighting applied to the at least one X-ray image.

11. The X-ray system according to claim 10, wherein the determined associated energy-dependent weighting is employed for detecting the tissue structure of interest by employing an energy-dependent visibility of a certain tissue structure of interest.

12. The X-ray system according to claim 6, wherein the at least one electronic processor is further programmed to one of:
    perform first a computer aided detection algorithm and second a spectral evaluation on an X-ray image;
    perform first a spectral evaluation and second a computer aided detection algorithm on an X-ray image; and
    perform a combined spectral computer aided detection algorithm on an X-ray image.

13. The non-transitory computer-readable medium according to claim 8, further comprising
    determining a plurality of further X-ray images, each further X-ray image having an individual defined energy-dependent weighting; and
    evaluating the plurality of further X-ray images for detecting the tissue structure shape; and
    determining from the plurality of further X-ray images at least one X-ray image by optimizing or minimizing visibility for a certain tissue structure shape.

14. The non-transitory computer-readable medium according to claim 8, wherein determining from the plurality of further X-ray images at least one X-ray image by optimizing or minimizing visibility for a certain tissue structure shape comprises determining an associated energy-dependent weighting applied to the at least one X-ray image.

15. The non-transitory computer-readable medium according to claim 14, wherein the determined associated energy-dependent weighting is employed for detecting the tissue structure of interest, in particular by employing an energy-dependent visibility of a certain tissue structure of interest.

16. The non-transitory computer-readable medium according to claim 8, wherein the computer aided detection comprises one of performing first a computer aided detection algorithm and second a spectral evaluation on an X-ray image, performing first a spectral evaluation and second a computer aided detection algorithm on an X-ray image, and performing a combined spectral computer aided detection algorithm on an X-ray image.

17. The method of claim 1, wherein the energy-dependent weighting is one of a band pass weighting, a low pass weighting, a high pass weighting and a notch weighting.

18. The X-ray system of claim 6, wherein the energy-dependent weighting is one of a band pass weighting, a low pass weighting, a high pass weighting and a notch weighting.

19. The non-transitory computer-readable medium of claim 8, wherein the energy-dependent weighting is one of a band pass weighting, a low pass weighting, a high pass weighting and a notch weighting.

* * * * *